United States Patent [19]

Taylor

[11] 4,147,170
[45] Apr. 3, 1979

[54] CATHETER WITH INFLATION CONTROL DEVICE

[75] Inventor: Glenn N. Taylor, Cary, Ill.

[73] Assignee: The Kendall Company, Boston, Mass.

[21] Appl. No.: 846,292

[22] Filed: Oct. 28, 1977

[51] Int. Cl.² ............................................. A61M 25/00
[52] U.S. Cl. ............................. 128/349 BV; 128/351
[58] Field of Search ............ 128/274, 349 B, 349 BV, 128/351; 137/226, 493, 853

[56] References Cited

U.S. PATENT DOCUMENTS

| 2,743,737 | 5/1956 | Textor | 137/493 |
| 3,108,610 | 10/1963 | De See | 137/493 |
| 3,631,877 | 1/1972 | Barosko | 137/493 X |
| 3,985,141 | 10/1976 | Stanley, et al. | 128/351 |
| 4,064,882 | 12/1977 | Johnson, et al. | 128/351 |
| 4,116,201 | 9/1978 | Shah | 128/351 |

*Primary Examiner*—Dalton L. Truluck
*Attorney, Agent, or Firm*—Powell L. Sprunger

[57] ABSTRACT

A catheter comprising, an elongated shaft, an inflatable balloon secured to the shaft, and an inflation lumen extending along the shaft and communicating with the balloon. The catheter has an inflation control assembly comprising a housing having a chamber, and a control member projecting into the chamber and having a circumferential sealing surface. The control assembly has a generally tubular valve element of flexible material having a sealing portion biased against the sealing surface. The valve element normally prevents passage of fluid through the housing, and flexes away from the sealing surface to permit inflation of the balloon. The valve element also flexes away from the sealing surface at a predetermined pressure in order to relieve pressure in the inflated balloon when overinflated.

17 Claims, 5 Drawing Figures

U.S. Patent    Apr. 3, 1979    4,147,170
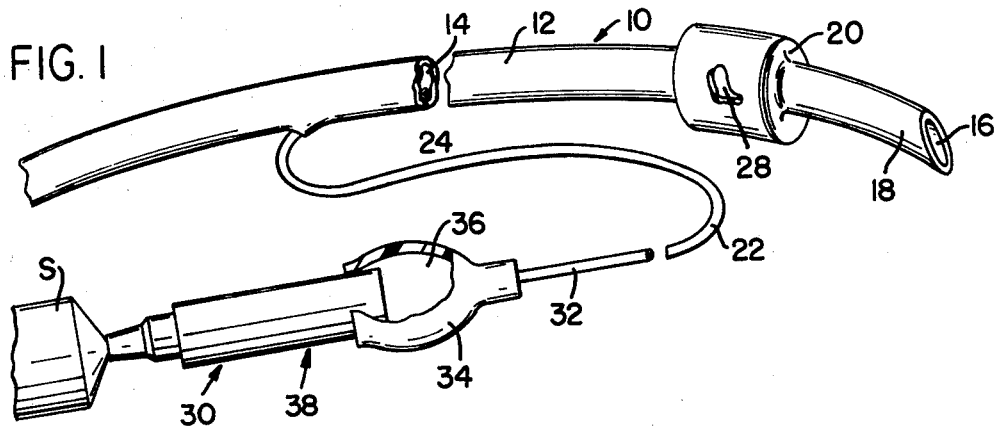
FIG. 1
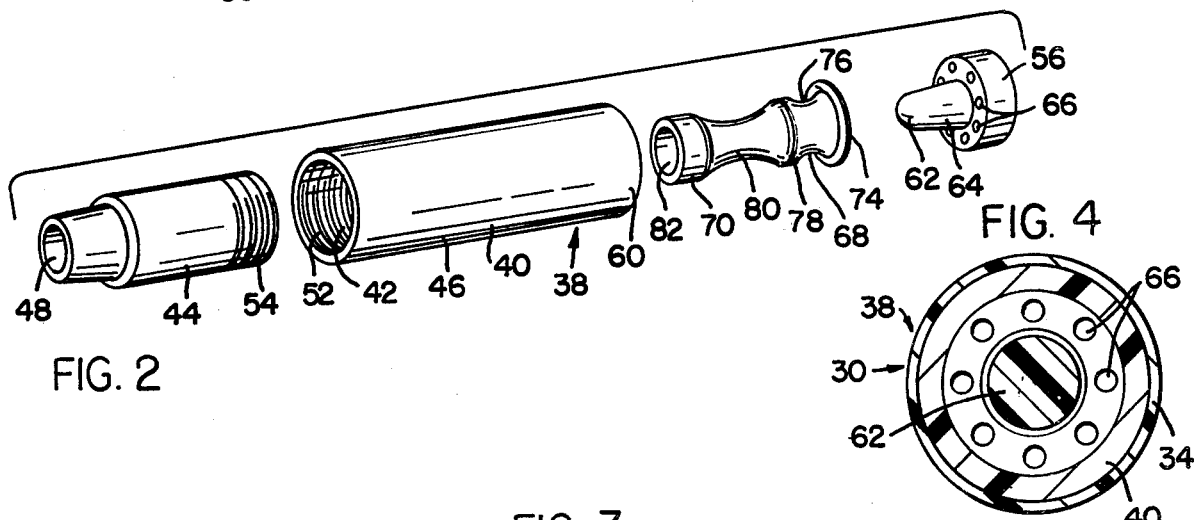
FIG. 2
FIG. 4
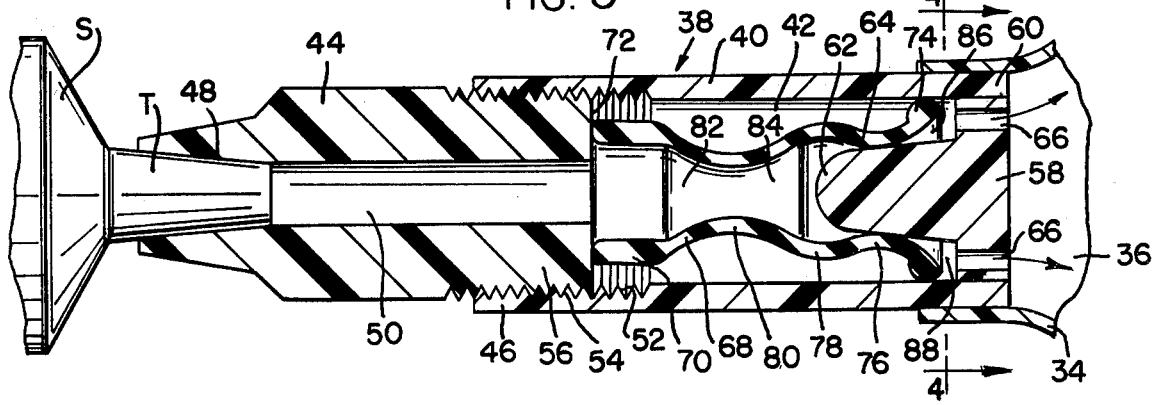
FIG. 3
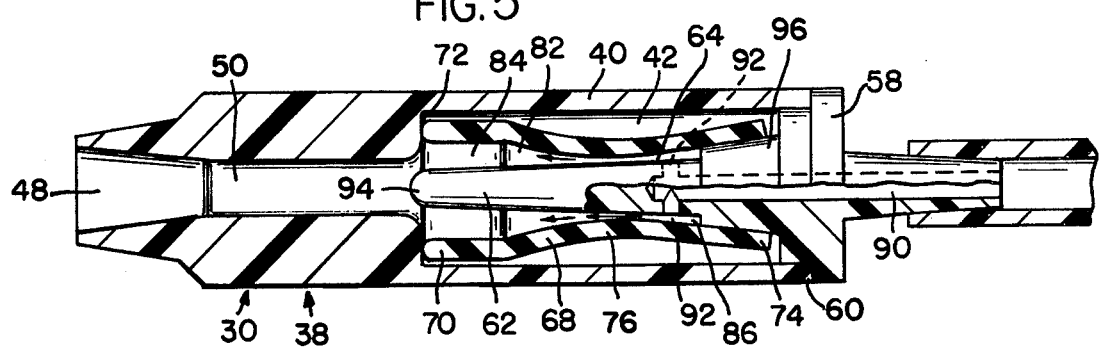
FIG. 5

CATHETER WITH INFLATION CONTROL DEVICE

BACKGROUND OF THE INVENTION

The present invention relates to catheters, and more particularly to inflation control devices for such catheters.

A various assortment of catheters, such as endotracheal tubes and Foley catheters, have been proposed for use on patients. Such catheters are normally constructed with a shaft having a main lumen, an inflatable balloon secured to a distal end of the shaft, and an inflation lumen extending through a side arm of the catheter and along the shaft, with the inflation lumen communicating with the balloon. The catheters are normally provided with a valve on the side arm, which is located outside the patient during use of the catheter, in order to control inflation and deflation of the balloon. Although such catheters are in common use, a persistent problem with catheters has been determining an accurate inflation pressure in the balloon.

In the case of endotracheal tubes, the balloon or cuff if properly inflated seals off the trachea and retains the endotracheal tube in place. If the balloon has been inflated to a pressure less than the necessary amount, then the positive pressures developed by a respirator during use of the endotracheal tube may cause loss of seal by the cuff. On the other hand, if the cuff is overinflated, the contact of the cuff against the trachea frequently results in pressure necrosis of the tracheal mucosa. Thus, it is necessary that the cuff or balloon be inflated to a pressure sufficient to maintain a seal in the trachea, yet sufficiently small to minimize the possibility of necrosis. Of course, the inflated balloon is not directly visible to the physician, but even if visible, it is difficult to determine whether or not the balloon has been inflated to the desired pressure.

SUMMARY OF THE INVENTION

A principal feature of the present invention is the provision of an inflation control device for a catheter.

The catheter comprises, an elongated shaft, an inflatable balloon secured to the shaft, and an inflation lumen extending along the shaft and communicating with the balloon. The catheter has an inflation control assembly comprising, a housing having an inflation port, a chamber, a control member projecting into the chamber and having a circumferential sealing surface, and opening means communicating between the chamber and inflation lumen. The control assembly has a generally tubular valve element of flexible material having spaced first and second portions sealingly engaged against the housing and defining a channel intermediate the first and second portions in the chamber. The control member is received in the valve element channel, and the valve element has a sealing portion circumferentially biased against and sealingly engaging against the sealing surface of the control member. The sealing portion separates a first section of the channel communicating with the inflation port from a second section of the channel communicating with the opening means.

A feature of the present invention is that the valve element normally prevents passage of fluid between the inflation port and opening means while the sealing portion is sealingly engaged against the sealing surface.

Another feature of the invention is that the sealing portion flexes away from the sealing surface responsive to pressure in the first channel section to permit passage of fluid from the inflation port to the opening means.

Thus a feature of the present invention is that the control assembly permits inflation of the balloon during which the sealing portion of the valve element flexes away from the sealing surface.

A further feature of the invention is that the sealing portion flexes away from the sealing surface responsive to a predetermined pressure in the balloon and the opening means to permit passage of fluid from the opening means to the inflation port.

Thus, a feature of the invention is that the control assembly automatically relieves pressure in the balloon in the event that it has been inflated to a pressure above the predetermined pressure.

Another feature of the invention is that the balloon may be purposely overinflated in order to actuate the control assembly after inflation of the balloon.

Accordingly, a feature of the present invention is that the inflation control assembly may be utilized to establish a relatively accurate final pressure in the inflated balloon which is required to maintain a seal of the balloon against the trachea and minimize the possibility of pressure necrosis.

Still another feature of the invention is the provision of means for modifying the predetermined pressure at which the valve element actuates responsive to overinflation of the balloon.

Further features will become more fully apparent in the following description of the embodiments of this invention and from the appended claims.

DESCRIPTION OF THE DRAWINGS

In the drawings:

FIG. 1 is a fragmentary perspective view, partly broken away, of an endotracheal tube having an inflation control device according to the present invention.

FIG. 2 is an exploded perspective view of the control device of the present invention;

FIG. 3 is a sectional view of the control device of FIG. 2;

FIG. 4 is a sectional view taken substantially as indicated along the line 4—4 of FIG. 3; and FIG. 5 is an elevational view, taken partly in section, of another embodiment of the control device of the present invention.

DESCRIPTION OF THE PREFERRED EMBODIMENTS

Referring now to FIG. 1, there is shown an endotracheal tube or catheter generally designated 10 having an elongated shaft or tube 12, a main lumen 14 extending through the shaft 12, an opening 16 adjacent a distal end 18 of the shaft 12, and an inflatable balloon or cuff 20 secured to and surrounding the shaft 12 adjacent the distal end 18 of the shaft. The endotracheal tube 10 has a side arm 22, and an inflation lumen 24 extending through the side arm 22 and through a wall of the shaft 12, with the inflation lumen communicating through an opening in the shaft 12 with a cavity 28 intermediate the balloon 20 and shaft 12. The endotracheal tube 10 also has an inflation control device or assembly generally designated 30 secured to an outer end 32 of the side arm 22 by any suitable means, such as a flexible sleeve 34 connected between the device 30 and the side arm 22 to establish communication between the device 30 and inflation lumen 24 through a cavity 36 in the sleeve 34. As will be further discussed below, a syringe S is utilized to pump fluid through the inflation control device 30, the inflation lumen 24 and into the cavity 28 in order to inflate the balloon 20, and the syringe S may be utilized to deflate the balloon 20 by withdrawing the fluid from the cavity 28 through the inflation lumen 24 and control device 30. Although, for convenience, the inflation control device 30 will be described primarily in connection with an endotracheal tube, it will be understood that the inflation control device may be utilized on any suitable catheter or similar device, such as a Foley catheter.

With reference to FIGS. 2–4, the inflation control device or assembly 30 has a housing 38 having an outer cylindrical wall or casing 40 partially defining a chamber 42. The housing 38 has a plug 44 received in a proximal end 46 of the casing 40 and defining a proximal end of the chamber 42. The plug 44 has a tapered inflation port 48 to receive a tip T of the syringe S, and a bore 50 extending through the remainder of the plug 44 and communicating between the inflation port 48 and the chamber 42. As shown, the casing 40 and plug 44 have cooperating threads 52 and 54, respectively, at an inner surface of the casing 40 adjacent the proximal end 46 of the casing 40 and on the outer surface of the plug 44 adjacent a distal end 56 thereof. The threads 52 and 54 of the casing and plug permit adjustment of the longitudinal position of the plug in the casing 40 for a purpose which will be described below. The housing 38 also has an end member 58 secured to a distal end 60 of the casing 40. As shown, the end member 58 has a generally conically shaped control member 62 projecting proximally in the chamber 42 and defining a proximally tapered outer surface of the control member 62 including a circumferential sealing surface 64 located intermediate opposed ends of the control member 62. The end member 58 also has a plurality of openings or opening means 66 extending through a wall of the end member 58 and communicating between the chamber 42 and the cavity 36 of the sleeve 34 and thus with the inflation lumen of the endotracheal tube.

The control device 30 also has a generally tubular valve element 68 of flexible and elastic material, such as rubber, received in the chamber 42. The valve element 68 has a first end portion 70 bearing against and sealingly engaging with a distal wall 72 of the plug 44 peripherally around a distal end of the bore 50. The valve element has an outwardly flared second end portion 74 which sealingly engages against an inner surface of the casing 40 adjacent the distal end 60 thereof. The valve element 60 has a sealing portion 76 adjacent the second end portion 74 and having a diameter less than the diameter of the second portion 74. The sealing portion 76 is circumferentially biased against and sealingly engages against the sealing surface 64 of the control member 62. The valve element 68 has a third portion 78 located adjacent the sealing portion 76 and intermediate the sealing portion 76 and the first end portion 70, with the third portion 78 having a diameter greater than the diameter of the sealing portion 76 and a diameter approximately equal to the diameter of the first end portion 70. The valve element 68 also has a fourth portion 80 located intermediate the first portion 70 and the third portion 78 and having a diameter less than the diameter of the sealing portion 76, such that the fourth portion 80 has the smallest diameter of the various portions in the valve element 68.

The valve element 68 defines a channel 82 intermediate the opposed end portions 70 and 74, with the control member 62 being received in the channel 82 of the valve element 68. The sealing portion 76 of the valve element 68 separates a first section 84 of the channel 82 which communicates with the plug bore 50 and inflation port 48 from a second section 86 of the channel 82 which communicates with the openings 66. Thus, the valve element 68 closes the chamber 42 intermediate the sealing surface 64 of the control member 62 and the plug bore 50, and intermediate the sealing surface 64 and the inner surface of the casing 40, such that a distal portion 88 of the chamber 42 which communicates with the openings 66 is closed from the remainder of the chamber.

Since the sealing portion 76 of the valve element 68 sealingly engages against the sealing surface 64 of the control member 62, the valve element 68 normally prevents passage of fluid between the inflation port 48 and the opening means 66. However, when the syringe tip T of the syringe S is placed in the inflation port 48, and the syringe is pumped, the pressure generated by the syringe causes the sealing portion 76 of the valve element 68 to flex away from the sealing surface 64 of the control member 62 in order to permit passage of fluid from the syringe between the sealing surface 64 and the sealing portion 76 of the valve element 68. In this manner, fluid may be pumped by the syringe through the valve element 68 and the openings 66 into the inflation lumen of the endotracheal tube in order to inflate the cuff or balloon. Once the cuff has been inflated, the syringe is removed from the control device 30, and the sealing portion 76 of the valve element 68 again assumes its sealing configuration against the sealing surface 64 of the control member 62 to prevent passage of fluid through the control device 30. However, in the event that the cuff has been inflated above a predetermined pressure, as determined by the valve element 68, the pressure in the cuff causes the sealing portion 76 of the valve element 68 to again flex away from the sealing surface 64 of the control member 62 in order to permit passage of fluid from the cuff through the inflation lumen and the openings 66 and past the sealing surface 64 between the valve element and control member in order to relieve pressure in the cuff. Once the predetermined pressure has been obtained in the cuff, the sealing portion 76 of the valve element 68 again flexes against the sealing surface 64 of the control member 62 to prevent further passage of fluid from the cuff past the valve element 68. In this manner, a desired predetermined pressure may be achieved in the cuff which is required to maintain a seal of the cuff against the trachea and yet which minimizes the possibility of pressure necrosis due to overinflation of the cuff.

The predetermined pressure at which the control device actuates to relieve pressure in the cuff may be partially controlled by the durometer hardness of the valve element 68 itself. In addition, in a preferred form, the valve element 68 is longitudinally compressed a desired amount in the chamber 42 in order to control the amount of bias of the sealing portion 76 against the sealing surface 64 of the control member 62, and thus control the pressure in the cuff which causes actuation of the valve element 68 after inflation. As previously discussed, the cooperating threads 52 and 54 of the casing 40 and plug 44 permit longitudinal adjustment of the plug 44 in the casing 40. Thus, the longitudinal position of the plug 44 relative the casing 40 may be modified to increase or decrease the longitudinal compression of the valve element 68 and modify the predetermined pressure at which the valve element 68 actuates responsive to overinflation of the cuff. In this manner, the plug may be adjusted in order to achieve a relatively accurate desired final pressure in the cuff. Of course, it will be apparent that the cuff of the endotracheal tube may be purposely overinflated, and, after the syringe is removed from the control device 30, the overinflated cuff automatically actuates the valve element 68 to relieve pressure in the cuff and establish the desired final pressure. Accordingly, the control device of the present invention permits the user to obtain a final accurate pressure in the cuff which is sufficient to obtain the necessary seal in the trachea, and yet minimize the possibility of pressure necrosis.

Another embodiment of the present invention is illustrated in FIG. 5, in which like reference numerals designate like parts. In this embodiment, the end member 58 has an elongated tapered control member 62 extending substantially the length of the chamber 42. The end member 58 also has a passageway 90 which communicates with the inflation lumen of the endotracheal tube and which communicates with the outer surface of the control member 62 at a pair of opposed openings 92. The valve element 68 has a sealing portion 76 intermediate the opposed end portions 70 and 74 and having a reduced diameter relative the diameter of the end portions 70 and 74. The sealing portion 76 sealingly engages against a circumferential sealing surface 64 on the control member 62 intermediate the openings 92 and a proximal end 94 of the control member 62. The second end portion 74 of the valve element 68 sealingly engages against an annular flange 96 of the control element 62 adjacent a distal end thereof, such that the second channel section 86 is located intermediate the sealing surface 64 and the flange 96. As before, the first channel section 84 of the valve element 68 communicates with a bore 50 and inflation port 48 of the housing, with the inflation port 48 being tapered and of a size to receive a syringe tip.

The sealing portion 76 of the valve element 68 sealingly engages against the sealing surface 64 of the control member 62 and normally prevents passage of fluid between the inflation port 48 and the openings 92 of the control member 62. However, when a syringe is attached to the control device 30 and is pumped, the pressure generated by the syringe causes the sealing portion 76 of the valve element 68 to flex away from the sealing surface 64 and permit passage of fluid between the sealing portion 76 and the sealing surface 64 in order to inflate the cuff. After the cuff has been inflated, the syringe is removed from the control device, and the sealing portion 76 assumes its sealing configuration against the sealing surface 64. However, in the event that the cuff has been inflated above the predetermined pressure, the pressure in the cuff causes actuation of the valve element 68, such that the sealing portion 76 of the valve element 68 flexes away from the sealing surface 64 of the control member 62 to permit passage of fluid from the cuff through the openings 92 and past the sealing portion 76. In this manner, the pressure in the cuff is relieved until the final predetermined pressure in the cuff has been obtained, after which the sealing portion 76 of the valve element 68 again flexes against the sealing surface 64 of the control member 62 to prevent further passage of fluid through the control device. In this manner, a relatively accurate final pressure may be established in the cuff.

The foregoing detailed description is given for clearness of understanding only, and no unnecessary limitations should be understood therefrom, as modifications will be obvious to those skilled in the art.

I claim:

1. A catheter, comprising:
   an elongated shaft;
   an inflatable balloon secured to the shaft;
   an inflation lumen extending along the shaft and communicating with the balloon; and
   an inflation control assembly comprising,
      a housing having an inflation port, a chamber, a control member projecting into said chamber and having a circumferential sealing surface, and opening means communicating between the chamber and inflation lumen, and
      a generally tubular valve element of flexible material having spaced first and second portions sealingly engaged against the housing and defining a channel intermediate said first and second portions in the chamber, said control member being received in the valve element channel, said valve element having a sealing portion circumferentially biased against and sealingly engaging against said sealing surface of the control member, said sealing portion separating a first section of the channel communicating with said inflation port from a second section of the channel communicating with the opening means, said valve element normally preventing passage of fluid between the inflation port and opening means while said sealing portion is sealingly engaged against said sealing surface, said sealing portion flexing away from the sealing surface responsive to pressure in the first channel section to permit passage of fluid from the inflation port to the opening means and inflate the balloon, and said sealing portion flexing away from the sealing surface responsive to a predetermined pressure in the opening means to permit passage of fluid from the opening means to the inflation port and relieve pressure in the inflated balloon.

2. The catheter of claim 1 wherein said control member extends from a distal portion of the housing proximally in said chamber.

3. The catheter of claim 2 wherein said control member has a generally conical shape defining an outer surface generally tapered proximally along the control member.

4. The catheter of claim 2 wherein said second portion of the valve element is sealingly engaged against a distal portion of the control member, and in which the opening means includes a passageway extending through the distal portion of the control member and communicating with the second channel section at an opening in the control member located intermediate said second and sealing portions of the valve element.

5. The catheter of claim 2 wherein the housing includes an outer wall defining a portion of the chamber, and in which said second portion of the valve element comprises an outwardly flared end section of the valve element sealingly engaged against an inner surface of said housing outer wall.

6. The catheter of claim 5 wherein said control member extends from a distal wall of the housing, in which the valve element closes a distal portion of the chamber intermediate said sealing surface and the housing outer wall, and in which said opening means is located in said distal wall adjacent the control member.

7. The catheter of claim 1 wherein said sealing portion of the valve element has a reduced diameter relative the diameter of the valve element on opposed longitudinally adjacent sides of the sealing portion.

8. The catheter of claim 1 wherein said housing has a bore communicating between said inflation port and said first channel section.

9. The catheter of claim 8 wherein said first portion of the valve element sealingly engages against a wall of the housing peripherally around a distal end of said bore.

10. The catheter of claim 1 wherein said valve element is longitudinally compressed in said chamber.

11. The catheter of claim 1 wherein said sealing portion of the valve element has a reduced diameter relative the diameter of said first and second valve element portions.

12. The catheter of claim 1 wherein said sealing portion of the valve element is located adjacent the second valve element portion and has a reduced diameter relative the diameter of said second portion, in which said valve element has a third portion located adjacent said sealing portion intermediate the sealing portion and said first valve element portion, with said third portion having a diameter greater than the diameter of the sealing portion, less than the diameter of said second portion, and approximately equal to the diameter of the first portion, and in which the valve element has a fourth portion located intermediate said first and third portions and having a diameter less than the diameter of the sealing portion.

13. The catheter of claim 1 including means for adjusting the pressure at which the sealing portion of the valve element releases from said sealing surface.

14. The catheter of claim 13 wherein the adjusting means comprises means for controlling the bias of said sealing portion against the sealing surface.

15. The catheter of claim 13 wherein the adjusting means comprises means for longitudinally compressing the valve element in said chamber, and means for modifying the compression of said valve element.

16. The catheter of claim 15 wherein said compressing means comprises a plug received in the housing and bearing against said first portion of the valve element, and in which the modifying means comprises means for controlling the longitudinal position of said plug in the housing.

17. The catheter of claim 16 wherein said controlling means comprises cooperating threads on said plug and on a wall of the housing.

* * * * *